US007351245B2

(12) United States Patent
Rozinsky et al.

(10) Patent No.: US 7,351,245 B2
(45) Date of Patent: Apr. 1, 2008

(54) APPARATUS AND METHOD FOR DISLODGING OBJECT FROM THROAT

(76) Inventors: Bernice Joy Rozinsky, 46 Farmingdale Rd., Blooming Grove, NY (US) 10914; Saul D. Rozinsky, 46 Farmingdale Rd., Blooming Grove, NY (US) 10914

( * ) Notice: Subject to any disclaimer, the term of this patent is extended or adjusted under 35 U.S.C. 154(b) by 392 days.

(21) Appl. No.: 10/946,040

(22) Filed: Sep. 21, 2004

(65) Prior Publication Data

US 2006/0064111 A1   Mar. 23, 2006

(51) Int. Cl.
*A61B 17/50* (2006.01)
(52) U.S. Cl. ..................................... 606/106
(58) Field of Classification Search ............... 606/106; 128/205.19
See application file for complete search history.

(56) References Cited

U.S. PATENT DOCUMENTS

| | | | |
|---|---|---|---|
| 2,428,451 A | 10/1947 | Emerson | 128/29 |
| RE24,193 E | 8/1956 | Emerson | 128/29 |
| 3,939,830 A | 2/1976 | da Costa | 128/145.7 |
| 4,518,258 A | 5/1985 | Broersma | 356/405 |
| 4,527,897 A | 7/1985 | Okabe | 356/407 |
| 4,662,367 A | 5/1987 | Gore, Jr. | 128/202.28 |
| 4,677,289 A | 6/1987 | Nozaki et al. | 250/226 |
| 4,678,338 A | 7/1987 | Kitta et al. | 356/402 |
| 4,790,818 A | 12/1988 | DeLuca | 604/54 |
| 4,834,541 A | 5/1989 | Yamaba | 356/406 |
| 4,838,697 A | 6/1989 | Kurandt | 356/406 |
| 4,878,756 A | 11/1989 | Stauffer | 356/406 |
| 4,886,366 A | 12/1989 | Kogure | 356/406 |
| 4,917,500 A | 4/1990 | Lugos | 356/406 |
| 4,934,360 A | 6/1990 | Heilbron | 128/205.16 |
| 4,971,053 A | 11/1990 | Tarrats | 128/205.19 |
| 5,049,985 A | 9/1991 | Outa | 358/76 |
| 5,073,345 A | 12/1991 | Scott | 422/70 |
| 5,083,868 A | 1/1992 | Anderson | 356/402 |
| 5,091,642 A | 2/1992 | Chow et al. | 250/226 |
| 5,150,174 A | 9/1992 | Ryczek et al. | 356/402 |
| 5,609,149 A | 3/1997 | Takach | 128/200.24 |
| 5,628,305 A | 5/1997 | Melker | 128/202.29 |
| 5,680,220 A | 10/1997 | Delignieres | 356/406 |
| 5,754,283 A | 5/1998 | Keane et al. | 356/73 |

(Continued)

FOREIGN PATENT DOCUMENTS

DE   3717657   12/1988

(Continued)

*Primary Examiner*—Michael Thaler
(74) *Attorney, Agent, or Firm*—Steven Horowitz

(57) ABSTRACT

An apparatus for sucking out an object stuck in a person's throat, comprising hollow first and second bellows elements each having an orifice with a one-way valve and an exit valve, a tube structure comprising first and second legs having free distal ends outside the first and second bellows element respectively and proximal ends extending into at least the respective orifices, the first leg and the second leg joined at their respective free distal ends to form a double hose having a pliable sealing structure integral thereto at a distal end to seal the trachea and esophagus, and a handle element connected to a top portion of the first and second bellows elements to contract the first and second bellows elements. When the handle is released a sucking of air through the tube structure occurs and the first and second bellows elements expand back to their original size.

6 Claims, 4 Drawing Sheets

U.S. PATENT DOCUMENTS

| | | | |
|---|---|---|---|
| 5,769,072 A * | 6/1998 | Olsson et al. | 128/205.13 |
| 5,782,837 A | 7/1998 | York | 606/106 |
| 5,844,680 A | 12/1998 | Sperling | 356/303 |
| 5,949,549 A | 9/1999 | Voipio | 356/402 |
| 6,020,583 A | 2/2000 | Walowit et al. | 250/226 |
| 6,040,902 A | 3/2000 | Jung et al. | 356/73 |
| 6,094,272 A | 7/2000 | Okamoto | 356/402 |
| 6,157,454 A | 12/2000 | Wagner et al. | 356/407 |
| 6,262,804 B1 | 7/2001 | Friend et al. | 356/402 |
| 6,272,440 B1 | 8/2001 | Shakespeare et al. | 702/85 |
| 6,301,004 B1 | 10/2001 | Jung et al. | 356/73 |
| 6,305,818 B1 | 10/2001 | Lebens et al. | 362/184 |
| 6,462,819 B1 | 10/2002 | Terauchi et al. | 356/406 |
| 6,535,287 B1 | 3/2003 | Matsui et al. | 356/406 |
| 6,583,880 B2 | 6/2003 | Berstis | 356/407 |
| 6,603,551 B2 | 8/2003 | Mestha et al. | 356/402 |
| 6,614,530 B1 | 9/2003 | Duez et al. | 356/406 |
| 6,674,530 B2 | 1/2004 | Berstis | 356/406 |
| 6,707,553 B1 | 3/2004 | Imura | 356/402 |
| 6,741,351 B2 | 5/2004 | Marshall et al. | 356/406 |
| 2002/0036772 A1 | 3/2002 | Wagner et al. | 356/406 |
| 2002/0099387 A1 | 7/2002 | Gauderer et al. | 606/106 |
| 2003/0028158 A1 | 2/2003 | Litkouhi | 604/319 |
| 2003/0030808 A1 | 2/2003 | Marshall et al. | 356/406 |
| 2003/0071998 A1 | 4/2003 | Krupka | 356/402 |

FOREIGN PATENT DOCUMENTS

| | | |
|---|---|---|
| DE | 3717658 | 12/1988 |
| DE | 1007361 | 9/1991 |
| JP | 2003172658 | 6/2003 |
| WO | WO 02/093116 A1 | 11/2002 |

* cited by examiner

APPARATUS AND METHOD FOR DISLODGING OBJECT FROM THROAT

FIELD OF THE INVENTION

The field of this invention is apparatuses and methods for the removal of objects caught in someone's throat, and more particularly, a method and apparatus suitable for removing an object stuck in the trachea of an individual who is in danger of choking.

BACKGROUND OF THE INVENTION AND DISCUSSION OF THE PRIOR ART

It is well known that people get things caught in their throat and are in danger of choking. Although generally an object that is lodged in the trachea is more dangerous and could cause choking whereas an object that is lodged in the esophagus is less dangerous, onlookers do not know whether the object is lodged in the windpipe or the esophagus and either predicament requires immediate help. Restaurants, wedding halls, schools, hotels and countless other places would obviously love to have a solution to that.

The prior art includes aspirators used by medical service technicians that suck the object out. The disadvantage is it requires expertise since it involves inserting the aspirator down the throat to the point of the object. The other significant prior art is the Heimlich maneuver. The disadvantages of it are that not everyone knows of it and it requires some expertise, it requires a second person and it cannot be done on certain types of people such as very overweight people. A third type of prior art that has developed is patents describing various types of devices designed to suck objects out of the throat of a choking victim through a single tube. These devices have not been successful in the sense that there is no known device of this kind used regularly in a school, home, restaurant, hotel, catering hall, etc. Furthermore, the devices described in these patents are not easy to use in the context of an excited choking victim.

One problem with known devices is the time needed to establish a seal in the choking victim's pharynx when the victim is in an excited state. Attempts to address this problem in the prior art, such as by employing a seal at the mouth with a mask rather than relying on a seal at the throat, have not solved or even addressed the additional problem that the tube in the mouth might suck up materials from the esophagus rather than the object lodged in the trachea if the seal around the trachea is not effective. Furthermore, certain of these patents use a complicated system of creating a partial vacuum such as by a piston, spring and latch. None of these devices have become popular, as noted.

Accordingly, what is needed is a device that overcomes the disadvantages of the prior art and actually becomes popular in the sense of being located in countless schools, restaurants, catering halls, hotels and homes.

SUMMARY OF THE PRESENT INVENTION

An apparatus and method is provided for sucking out an object stuck in a person's throat. The apparatus comprises hollow first and second bellows elements each having an orifice with a one-way valve and an exit valve, a tube structure comprising first and second legs having free distal ends outside the first and second bellows element respectively and proximal ends extending into at least the respective orifices, the first leg and the second leg joined at their respective free distal ends to form a double hose having a pliable sealing structure at the distal end to seal the trachea and esophagus, and a handle element connected to a top portion of the first and second bellows elements to contract the first and second bellows elements. When the handle is released, a sucking of air through the tube structure occurs and the first and second bellows elements expand back to their original size.

In an alternative embodiment, the two bellows elements are vertically stacked rather than side by side.

IMPORTANT OBJECTS AND ADVANTAGES

The following important objects and advantages of the present invention are:

(1) to provide an apparatus that can dislodge an object stuck in someone's throat;

(2) to provide such an apparatus that employs a double hose to seal the pharynx;

(3) to provide such an apparatus that decreases the likelihood that an imperfect seal will fail to suck the object, if the object is in the trachea of the person;

(4) to provide such an apparatus that in one preferred embodiment employs two bellows elements operating in parallel;

(5) to provide such an apparatus, and a method employing said apparatus that is simple enough to be operated by a non-professional lifesaver including even a child lifesaver;

(6) to provide an apparatus for dislodging an object stuck in someone's throat that has a sealing structure that is designed to accommodate the fact that individuals have two pipes that extend from the back of the throat;

(7) to provide a simple and effective method of saving an individual choking from an object lodged in the individual's throat;

(8) to provide an apparatus for dislodging an object stuck in someone's throat that is of simple construction;

(9) to provide such an apparatus that in certain embodiments avoids the necessity of having springs and a piston;

(10) to provide such an apparatus that employs two bellows elements that suck independently of each other;

(11) to provide an apparatus having two bellows elements whereby a deficient seal of the hose emanating from a first bellows element will not disturb or undermine an otherwise effective seal of the hose emanating from the second bellows element;

(12) to provide a single apparatus including a tube structure that ends in a double hose;

(13) to provide a method employing such an apparatus that can operate effectively even if used improperly, that is even if the rescuer improperly places the double hose in the victim's throat prior to forcing air out of the bellows elements;

(14) to provide an apparatus and method using same that avoids the need to have a rescuer perform the task of placing an implement down the victim's throat; and

(15) to provide such an apparatus and method that need only be placed in the victim's pharynx.

DETAILED DESCRIPTION OF THE PREFERRED EMBODIMENT

Figure 1:
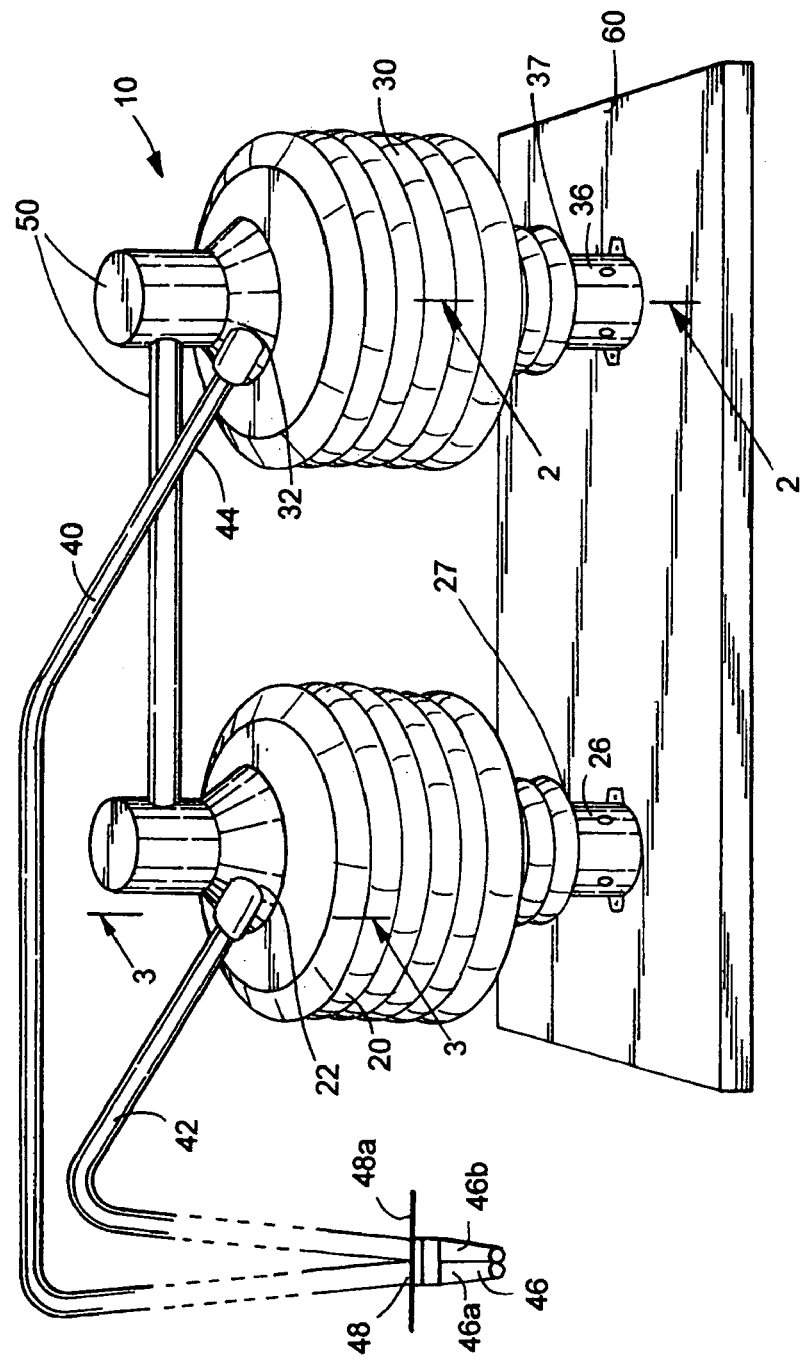
FIG. 1 is a perspective view of the apparatus of the present invention.

The apparatus of the present invention will now be illustrated by reference to the accompanying drawings. The apparatus of the present invention has been assigned reference numeral 10 Other elements have been assigned the reference numerals referred to below.

Figure 2:
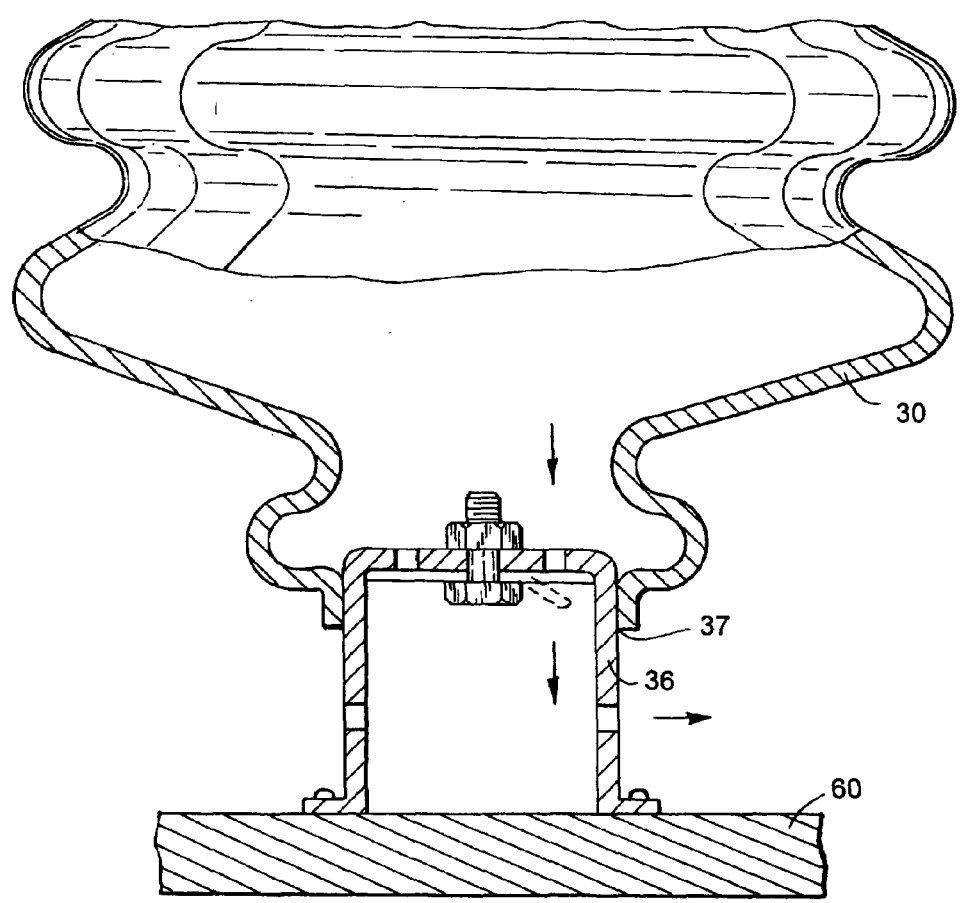
FIG. 2 is a vertical sectional view of FIG. 1 taken along line 2-2 of FIG. 1.
Figure 3:
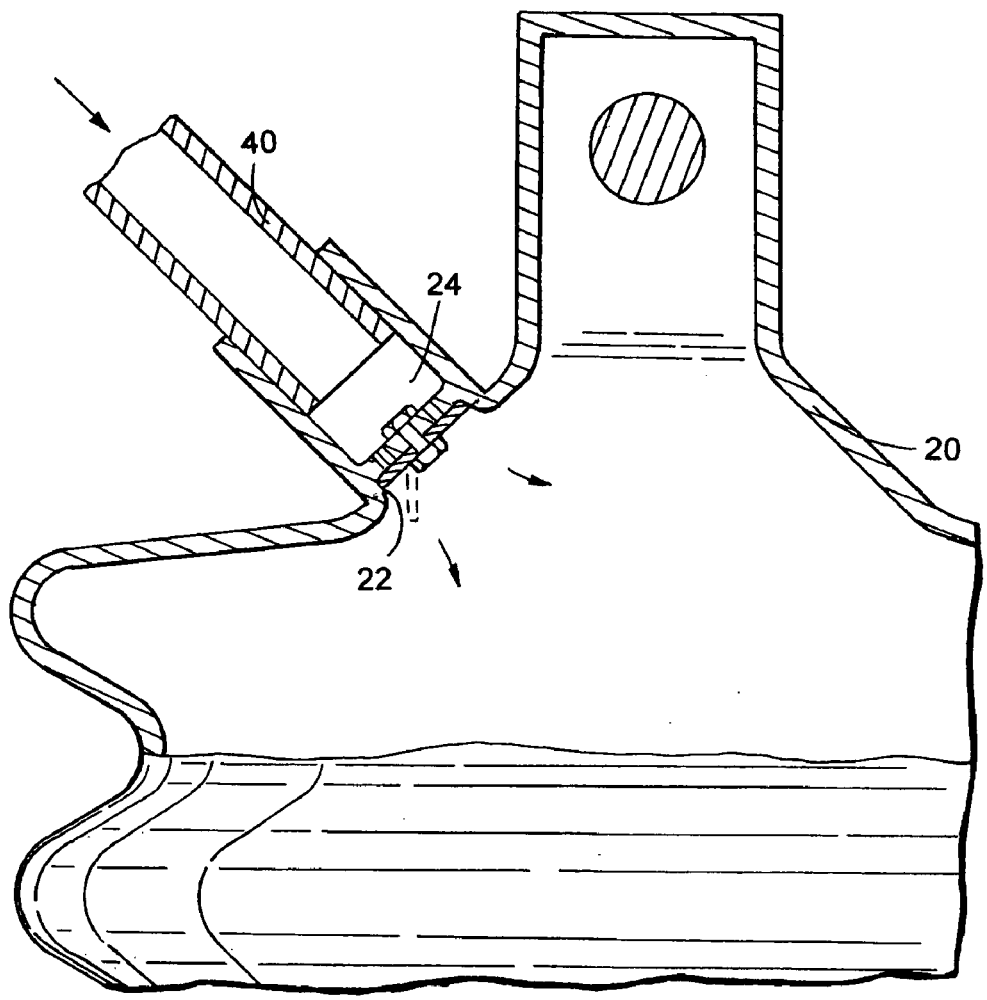
FIG. 3 is a vertical sectional view of FIG. 1 taken along line 3-3 of FIG. 1.

As seen from FIGS. 1-3, the present invention is an apparatus and method for sucking out an object dislodged in someone's trachea or esophagus. Since the method utilizes the apparatus of the present invention, the apparatus is first described.

In the present invention there is a double hose that is placed adjacent to the top of the two pipes of a person choking. This is accomplished by the use of a tube structure having at its free distal end a double hose, which provides an advantage. Recognizing that the pharynx seal is always difficult to do when the patient and/or helper are in an excited state, the double hose provide a partial solution to that problem. Because even if due to the choking victim being in an excited state the double hose is not positioned exactly right, and there is not a strong seal, there is still likely to be a better seal from the double hose than from a single hose or tube.

An inadequately sealed single tube may suction only from the esophagus if it is situated more over that pipe than over the trachea, thus leaving the victim no better or worse off than before. Note that an object caught in the esophagus is not precisely a choking problem although it can be painful and frightening. When attempting to seal the pharynx one wants to avoid suctioning only from the esophagus which could happen if you have only one tube and it is slightly misplaced. In that case, if there is true choking in the trachea occurring, the misplacement is dangerous. By having two hoses in a double hose formation, one of the hoses is in all likelihood going to be positioned and situated over and nearer to the trachea, so that it is much less likely for there to be a sucking up force situated only over the esophagus.

Furthermore, since the present invention makes use of two hoses at the point of the seal, it is preferable that the bellows element contain two separate chambers, a first chamber and a second chamber. Otherwise, if there is only one chamber in the bellows elements, if one of the hoses properly seals the trachea and the other hose improperly or imperfectly seals the esophagus or the rest of the pharynx, the imperfect seal will cause the loss of the vacuum in the bellows element since air would only enter the unsealed tube and the sealed tube would not do any sucking or lifting of the foreign object.

Figure 4:
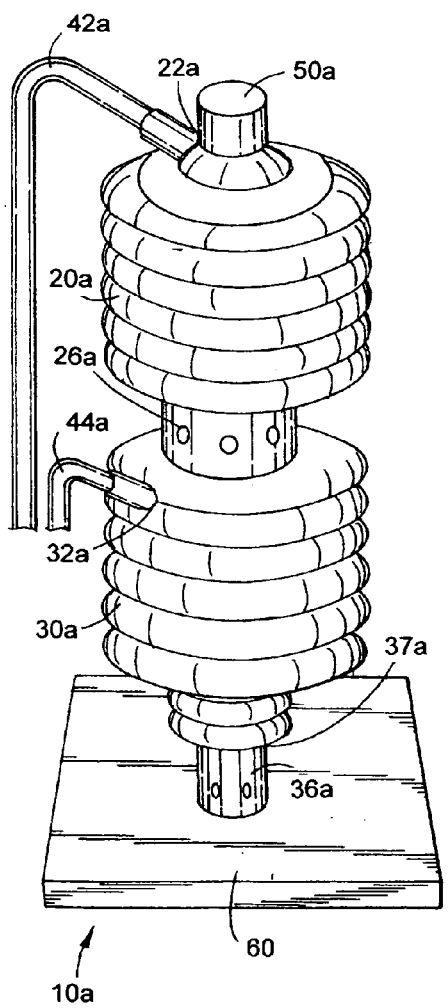
FIG. 4 is a perspective view of an alternative embodiment of the apparatus of the present invention with the tube structure truncated where the first and second bellows elements are vertically stacked.

Thus in a preferred embodiment there are two independent bellows elements, for example, a first bellows element and a second bellows element. While as seen in FIGS. 1-3, in a preferred embodiment, the first and second bellows elements are horizontally related with a common handle element. In an alternative embodiment, the first and second bellows elements are attached in a manner that causes the contraction of the first bellows element to cause the contraction of the second bellows element and the expansion of the first bellows element to cause the expansion of the second bellows element. As seen in FIG. 4, one example of such attachment is where the two bellows elements are vertically stacked so that the force on the top one transmits the same force to the bottom bellows element.

Thus, each bellows element has its own tube extending out of it through its own orifice so that if one of the two tubes does not form a seal it does not mean that the other one is affected by that deficiency.

In a preferred embodiment, the apparatus 10 for dislodging and sucking out an object stuck in a throat of a person, comprises a hollow first bellows element 20 having a first orifice 22, the first orifice 22 having a one-way valve 24 that prevents air from exiting the first bellows element 20 through the first orifice 22 and having a first one-way exit valve 26 at a first exit point 27 of the first bellows element 20 for air (or a gas) to leave the first bellows element 20 and apparatus 10 also includes a hollow second bellows element 30 having a second orifice 32, the second orifice 32 having a one-way valve 24 that prevents air from exiting the second bellows element 30 through the second orifice 32 and having a second one-way exit valve 36 at a second exit point 37 of the second bellows element 30 for air (or a gas) to leave the second bellows element 30. It is noted that the one-way valve 24 in second orifice 32 is not explicitly shown in the drawings but is identical to one-way valve 24 shown in FIG. 3.

As shown in FIG. 1, first and second bellows elements 20, 30 have accordion-like folds that facilitate the contraction of first and second bellows elements 20, 30 and thereby allow said first and second bellows elements 20, 30 to squeeze substantially all air out of their hollow interiors. It should be noted that the number of such folds is not critical and any number suitable to perform the task is acceptable.

As seen from FIGS. 1 and 2, the valve case of the first and second one-way exit valves 26, 36 in each of the first and second bellows elements 20, 30 can be fitted to the respective bellows element by any secure air-tight attachment. The valves shown in the apparatus 10 herein are diaphragm check valves but the present invention is by no means limited to such valves. Both the first and second one-way exit valves 26, 36 and the one-way valves 24 can be any effective check valve.

In addition there is a tube structure 40 comprising a first leg 42 having a free distal end outside the first bellows element 20 and a proximal end extending to at least the first orifice 22 (and preferably for stability and durability reasons further extending to some degree into the first bellows element 20) and comprising a second leg 44 having a free distal end outside the second bellows element 30 and a proximal end extending to at least the second orifice 32, the first leg 42 and the second leg 44 joined at their respective free distal ends to form a double hose 46, the double hose 46 having a soft pliable sealing structure 48 at the distal end of the double hose 46 to assist the double hose in sealing the trachea and esophagus of the choking person. At a suitable distance from the distal end of double hose 46 there is formed, integral with the double hose 46, a pliable sealing structure 48. It should be understood that the term "distal end of the double hose" is not to be taken literally and shall include positions near or adjacent to the literal distal end of the double hose 46.

In certain embodiments pliable sealing structure 48 is substantially perpendicular to double hose 46, in which case, the outer end 48a of sealing structure 48 would be bent over or flapped over to seal the pharynx. It is noted that in general, pliable sealing structure 48 may be any structure that one skilled in the art would use to help the double hose 46 form a seal around the end of the throat over the two pipes—the windpipe and the esophagus. An example would be a soft plastic disk shaped in the form of the end of a person's throat.

Preferably, the first and second leg 42, 44 should be joined so that double hose 46 should be at least six inches long. Alternatively, the double hose 46 can constitute a much greater length of tube structure. For example, the double hose 46 could exist along the entire length of the tube structure 40 that is outside of the first and second bellows elements 20, 30.

The diameter of each hose of double hose 46 in tube structure 40 tapers at their distal end so that for the last approximately two inches of each hose of double hose 46, the diameter of each such hose 46a, 46b in double hose 46 should be narrower than at the beginning of double hose 46 and should have a diameter of approximately one half inch or slightly greater. In any event, the diameter of each hose 46a, 46b of double hose 46 and throughout tube structure 40 must be big enough so that enough force can be generated by air moving through the hose in order to admit the obstruction into the tube structure 40

The apparatus 10 also includes a handle element 50 connected to a top portion of the first bellows element and to a top portion of the second bellows element so that when a force is applied to the handle element the first bellows element contracts from a first original size and the second bellows element contracts from a second original size and when said force is released a sucking of air through the tube structure occurs and the first bellows element expands back to the first original size and the second bellows element expands back to the second original size at the same time.

The handle element 50 of the present invention is not limited to that shown in the drawing figures herein. Rather any handle element 50 is acceptable so long as it enables the rescuer to easily push down on and contract both the first and second bellows elements 20, 30 simultaneously.

Preferably, the first orifice 22 is at or near the top portion of the first bellows element 22 and the second orifice 32 is at or near the top portion of the second bellows element 30. However, this is not required from the point of view of physics or vacuum-creating. Rather it is simply more convenient for the user. Hence, the present invention is not to be limited to a location of the first and second orifice 22, 32 at or near the top portion of the first and second bellows elements 20, 30. Furthermore, the first one-way exit valve 26 and first exit point 27 and the second one way exit valve 36 and second exit point 37, although typically at or near a bottom portion of the first and second bellows elements 20, 30 respectively, said exit valves and exit points can be anywhere along the walls of the first bellows element 20 and second bellows element 30. If the first one-way exit valve 26 and/or the second one-way exit valve 36 is/are not at or near the bottom of the respective bellows elements, then the bottom portion of first and second bellows elements 20, 30 would be molded with a flange to attach directly to the base.

Finally, the preferred embodiment of the apparatus of the present invention would include a solid base 60, for example of wood, on which the first and second bellows elements 20, 30 of apparatus 10 sit. This is simply to allow the forces being exerted against the first bellows element 20 and the second bellows element 30 to be uniform and effective. Alternatively, the apparatus can exist without base 60, in which case apparatus 10 would be placed on a solid surface by the rescuer.

In an alternative embodiment illustrating the vertical stacking of the two bellows elements, as shown in FIG. 4, the apparatus 10a of the present invention is comprised of a hollow first bellows element 20a having a first orifice 22a, the first orifice 22a having a one-way valve (not seen in FIG. 4 but identical to one-way valve 24 of the main embodiment shown in FIGS. 1-3) that prevents air from exiting the first bellows element 20a through the first orifice 22a, a first one-way exit valve 26a at a first exit point 26a of the first bellows element for air to leave the first bellows element, a hollow second bellows element 30a positioned under the first bellows element 20a and having a second orifice 32a, the second orifice 32a having a one-way valve (not seen in FIG. 4 but identical to one-way valve 24 of the main embodiment shown in FIGS. 1-3) that prevents air from exiting the second bellows element 30a through the second orifice 32a, a second one-way exit valve 36a at a second exit point 37a of the second bellows element 30a for air to leave the second bellows element, a tube structure comprising a first leg 42a having a free distal end outside the first bellows element and a proximal end extending to at least the first orifice and comprising a second leg 44a having a free distal end outside the second bellows element and a proximal end extending to at least the second orifice, the first leg 42a and the second leg 44a joined at their respective free distal ends to form a double hose, the double hose having a pliable sealing structure at a distal end of the double hose to help seal the trachea and the esophagus of the person. Note that the double hose is not shown in any of the alternative embodiments but in these alternative embodiments it is identical to double hose 46 of the embodiment shown in FIGS. 1-3.

There is also a handle element 50a connected to a top portion of the first bellows element so that when a force is applied to the handle element the first bellows element contracts from a first original size and when said force is released the first bellows element expands back to the first original size while a sucking of air through the tube structure occurs, the second bellows element being connected to the first bellows element so that when the first bellows element contracts from a first original size the second bellows element contracts from a second original size and so that when the first bellows element expands back to the first original size the second bellows element expands back to the second original size.

As stated, one example of the structure of this alternative apparatus is where the first bellows element 20a and the second bellows elements 30a are vertically stacked so that the force on the top one transmits the same force to the bottom bellows element. In that case, handle element 50a need only be connected to the first bellows element 20a. Special modification would probably be needed at the bottom portion of first bellows element 20a (located on top of second bellows element 30a) and at the top portion of second bellows element 30a (located below first bellows element 20a) so that the two bellows elements meet in a way that the force on first bellows element 20a is effectively transmitted to second bellows element 30a. Thus, the top portion of second bellows element 30a need not have the cylindrical projection shown in FIG. 1. This cylindrical projection is merely a portion of handle element 50 and need not be present on the lower bellows element. Furthermore, handle element 50a may be any convenient shape. Purely by way of example, handle element 50a may comprise a T-shaped rod including a vertical rod having at its top a horizontal crossbar. In the embodiments of apparatus 10a, 10b of FIGS. 4-6 there would be no need for handle element 50a or 50b to include a rod that is shaped and connected in the way the rod of handle element 50 shown in FIG. 1 is shaped and connected.

Figure 5:
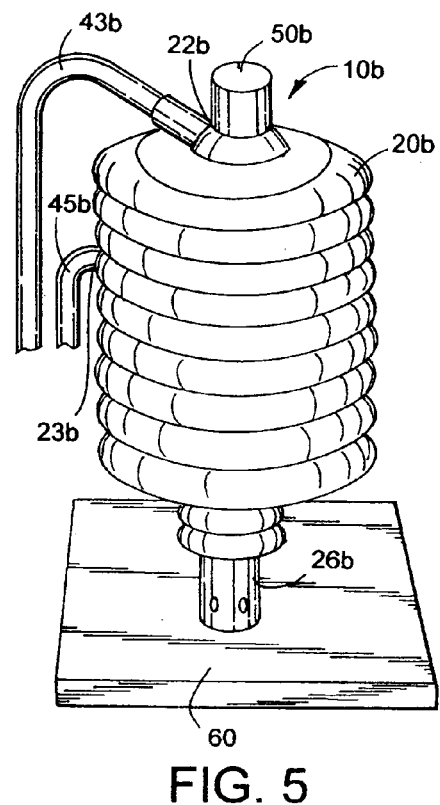
FIG. 5 is a perspective view of a further alternative embodiment of the apparatus of the present invention with the tube structure truncated wherein there is only a single bellows element having two orifices.

In a second further alternative embodiment of the present invention shown in FIG. 5, the apparatus 10b comprises a single bellows element 20b having two orifices and a tube structure. The tube structure is not explicitly seen in full in FIG. 5 since the twin hose portion 46 of the tube structure is cut off, but it is identical to the double hose shown in the embodiment of FIGS. 1-3. For example, the apparatus 10b would comprise a hollow bellows element 20b having a first orifice 22b and a second orifice 23b. The tube structure includes a first hose leg 43b having a distal end outside the bellows element 20b and a proximal end extending into at least the first orifice 22b and including a second hose leg 45b having a distal end outside the bellows element 20b and a proximal end extending into at least the second orifice 23b, the first hose leg 43b and the second hose leg 45b joined at their respective free distal ends to form a double hose (not shown) to seal a trachea and an esophagus of the person. As in all embodiments, each of the first and second orifices 22b, 23b have a one-way valve that prevents air from exiting the bellows element 20b through the first orifice 22b and through the second orifice 23b respectively. Bellows element 20b also has a one-way exit valve 26b at an exit point of the bellows element 20b for air to leave the bellows element. The double hose 46 has a pliable sealing structure at a distal end of the double hose to help seal the trachea and the esophagus of the person. A simple handle element 50b, i.e. any conveniently formed handle, is connected to a top portion of the bellows element 20b so that when a force is applied to handle element 50b the bellows element 20b contracts from an original size and when said force is released the bellows element 20b expands back to the original size while a sucking of air through the tube structure occurs.

Figure 6:
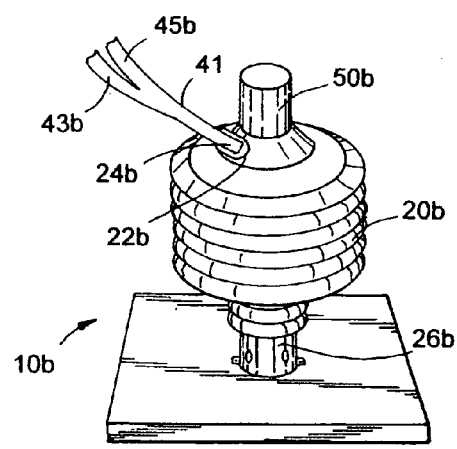
FIG. 6 is a perspective view of a second version of the alternative embodiment of FIG. 5 with the tube structure truncated where there is only one bellows elements and only one orifice.

In another version of the embodiment comprising one bellows element and one orifice and a Y-shaped tube structure (not seen), as shown in FIG. 6, the apparatus 10 comprises a hollow bellows element 20b having only one orifice 22b, the orifice 22b having a one-way valve 24b that prevents air from exiting the bellows element 20b through the orifice 22b, a one-way exit valve 26b at an exit point of the bellows element 20b for air to leave the bellows element 20b. A "Y" shaped tube structure includes a trunk 41 having a distal end outside the bellows element 20b and a proximal end extending at least into the orifice 22b and including a first hose leg 43b extending from the distal end of the trunk and a second hose leg 45b extending from the distal end of the trunk, the first hose leg 43b and the second hose leg 45b joined at their respective free distal ends to form a double hose, the double hose having a pliable sealing structure at a distal end of the double hose to help seal the trachea and the esophagus of the person. As in FIG. 5, the tube structure is cut off so that double hose 46 is also not seen in FIG. 6. There is a simple handle element 50b or any conveniently formed handle element, connected to a top portion of the bellows element so that when a force is applied to the handle element 50b the bellows element 20b contracts from an original size and when said force is released the bellows element 20b expands back to the original size while a sucking of air through the tube structure occurs.

Generally, in all embodiments, apparatus 10 includes a bellows-like element that creates a partial vacuum. Although technically the bellows element could be electrical or anything that generates a sucking effect, it is typically mechanical, as follows. As seen from FIG. 1, bellows elements 20, 30 are made of plastic and each forms a hollow container having an "accordion-shaped" outer surface. This makes it easy for a force applied from the top of the bellows element 20 to cause the bellows element to contract to the point where the air inside bellows element 20 has left. The user makes the bellows element 20 alternately contract and expand by pushing down on and releasing handle element 50.

In the method of the present invention, take the apparatus of the present invention, pushing down on the handle element and thereby causing (in the case of the preferred embodiment of the apparatus) the first bellows element and the second bellows element to simultaneously contract and thereby drive air out of the first and second bellows elements through the first and second one-way exit valves, insert the distal end of the double hose into a mouth of the choking victim so that the double hose seals the trachea and esophagus of the choking victim, let go of the handle element so as to allow the first bellows element and the second bellows element to expand by sucking air through the tube structure into the first and second bellows elements thereby dislodging the object, and repeat the pushing down on the handle and the letting go of the handle steps as many times as necessary. The apparatus' double hose should be removed after each compression and release to see if the apparatus has sucked out the object from the trachea.

Since the hoses 42, 44 including double hose 46 are plastic, they are washable with running water to maintain it clean and securely. Note that the rescuer depresses the bellows element(s) by simply pushing down on handle element 50 (or 50a or 5Ob) and then the double hose 46 is inserted into the patient's mouth but you do not have to put it down the throat. Just insert double hose 46 to the point of the pharynx, where the mouth narrows and goes into the throat. Use the pliable sealing structure to help seal the double hose over the two pipes of the person. Then release the bellows element(s), creating a sucking effect. Air further downstream from the stuck object rushes into the tubes trying to go in the direction of the bellows since the bellows' cavity is expanding. This rush of air dislodges the "caught object" in the same direction—namely out of the throat and into the mouth and then out of the mouth altogether.

The apparatus 10 has the important advantage in that a system of one-way valves assures that when depressing the bellows element the air leaving the bellows element exits through a designated opening and does not exit through the tube(s). For example, there is a one-way valve which may be located on the underside of the bellows element to assure that air exits at the underside of the bellows element(s) and cannot return into the bellows element(s) other than through the tubes. The safety feature is the presence of one-way valves at each orifice 22, 32 to ensure that air does not exit through the tube(s). Thus, if the nervous user puts the twin hose into position near the throat prior to depressing the bellows element, which is not correct since that could cause air to be pushed air into the throat if not for the safety feature, the air would not be pushed into the throat but would rather exit the bellows element through the exit adjacent to the one-way valve.

Note that even a child could operate this device. It requires no expertise. Taking into consideration the safety valve, you only have to know to do two things—put the hose in, push down on the bellows element and let go (although to do it properly you should first depress the bellows, then insert the hose and only then release the bellows.)

In a preferred embodiment, the bellows elements rest sturdily on base 60 or on a flat surface.

It should be noted that the "bellows element" in the present invention draws air in through the tube and expels it through a valve. Thus it differs slightly from the dictionary definition of a "bellows", which draws air in through a valve or orifice and expels it through a tube.

It is to be understood that while the apparatus of this invention have been described and illustrated in detail, the above-described embodiments are simply illustrative of the principles of the invention. It is to be understood also that various other modifications and changes may be devised by those skilled in the art which will embody the principles of the invention and fall within the spirit and scope thereof. It is not desired to limit the invention to the exact construction and operation shown and described. The spirit and scope of this invention are limited only by the spirit and scope of the following claims.

What is claimed is:

1. An apparatus for dislodging and sucking out an object stuck in a throat of a person, comprising:

a hollow first bellows element having a first orifice, the first orifice having a one-way valve that prevents air from exiting the first bellows element through the first orifice and having a first one-way exit valve at a first exit point of the first bellows element for air to leave the first bellows element, a hollow second bellows element having a second orifice, the second orifice having a one-way valve that prevents air from exiting the second bellows element through the second orifice and having a second one-way exit valve at a second exit point of the second bellows element for air to leave the second bellows element, a tube structure comprising a first leg having a distal end outside the first bellows element and a proximal end extending to at least the first orifice and comprising a second leg having a distal end outside the second bellows element and a proximal end extending to at least the second orifice, the first leg and the second leg joined at their respective distal ends to form a double hose, the double hose having a sealing structure at a distal end of the double hose to seal a trachea and an esophagus of the person, a handle element connected to a top portion of the first bellows element and to a top portion of the second bellows element so that when a force is applied to the handle element the first bellows element contracts from a first original size and the second bellows element contracts from a second original size and when said force is released a sucking of air through the tube structure occurs and the first bellows element expands back to the first original size and the second bellows element expands back to the second original size.

2. The apparatus of claim 1, including a solid base on which the first and second bellows elements sit.

3. The apparatus of claim 2, wherein the first orifice is at or near the top portion of the first bellows element.

4. The apparatus of claim 3, wherein the first exit point is at or near a bottom portion of the first bellows element.

5. The apparatus of claim 4, wherein the second orifice is at or near the top portion of the second bellows element.

6. The apparatus of claim 5, wherein the second exit point is at or near a bottom portion of the second bellows element.

* * * * *